(12) United States Patent
Huggins et al.

(10) Patent No.: US 8,071,844 B1
(45) Date of Patent: Dec. 6, 2011

(54) CULTIVATED MOMORDICA SPECIES AND EXTRACT THEREOF

(75) Inventors: William F. Huggins, Clearwater, FL (US); Konky Sotomayor, Palm Harbor, FL (US)

(73) Assignee: Nutritional Health Institute Laboratories, LLC, Tallahasse, FL (US)

( * ) Notice: Subject to any disclaimer, the term of this patent is extended or adjusted under 35 U.S.C. 154(b) by 200 days.

(21) Appl. No.: 12/211,089

(22) Filed: Sep. 15, 2008

Related U.S. Application Data

(60) Provisional application No. 60/972,165, filed on Sep. 13, 2007.

(51) Int. Cl.
 *A01H 5/00* (2006.01)
 *A61K 36/42* (2006.01)
(52) U.S. Cl. ......... 800/295; 424/725; 424/728; 800/298
(58) Field of Classification Search .................. None
 See application file for complete search history.

(56) References Cited

U.S. PATENT DOCUMENTS

| | | | |
|---|---|---|---|
| 4,084,010 A | 4/1978 | Takemoto et al. |
| 4,368,149 A | 1/1983 | Masuho et al. |
| 5,433,965 A | 7/1995 | Fischer et al. |
| 5,476,998 A | 12/1995 | Kataoka et al. |
| 5,484,889 A | 1/1996 | Lee-Huang et al. |
| 5,516,535 A | 5/1996 | Heckert et al. |
| 5,851,531 A | 12/1998 | Lazarus |
| 5,900,240 A | 5/1999 | Tomer et al. |
| 5,929,047 A | 7/1999 | Nakano |
| 5,942,233 A | 8/1999 | Chang |
| 6,103,240 A | 8/2000 | Zhou |
| 6,183,747 B1 | 2/2001 | Ren |
| 6,210,738 B1 | 4/2001 | Chen |
| 6,235,286 B1 | 5/2001 | Lazarus |
| 6,379,718 B2 | 4/2002 | Ren |
| 6,416,806 B1 | 7/2002 | Zhou |
| 6,562,379 B2 | 5/2003 | Lazarus |
| 6,682,766 B2 | 1/2004 | Blumenstein-Stahl et al. |
| 6,770,585 B2 | 8/2004 | Vuong |
| 6,800,726 B1 | 10/2004 | Rao et al. |
| 6,831,162 B2 | 12/2004 | Khanna |
| 6,960,348 B2 | 11/2005 | Rucker |
| 6,964,786 B1 | 11/2005 | Khanna |
| 6,986,906 B2 | 1/2006 | Selzer et al. |
| 7,014,872 B2 | 3/2006 | Pushpangadan et al. |
| 7,153,529 B2 | 12/2006 | Lazarus |
| 7,160,565 B2 | 1/2007 | Rifkin |
| 7,205,010 B2 | 4/2007 | Sha |
| 7,238,377 B2 | 7/2007 | Piccirilli et al. |
| 2002/0187232 A1 | 12/2002 | Lee et al. |
| 2003/0082168 A1 | 5/2003 | Yegorova |
| 2003/0165603 A1 | 9/2003 | Burklow et al. |
| 2003/0170365 A1 | 9/2003 | Huang |
| 2004/0058050 A1 | 3/2004 | Guo |
| 2004/0115329 A1 | 6/2004 | Tamiya et al. |
| 2005/0118324 A1 | 6/2005 | Mathew et al. |
| 2005/0152997 A1 | 7/2005 | Selzer et al. |
| 2006/0003053 A1 | 1/2006 | Ekanayake et al. |
| 2006/0040003 A1 | 2/2006 | Needleman et al. |
| 2006/0093685 A1 | 5/2006 | Mower et al. |
| 2006/0093686 A1 | 5/2006 | Yoshitome et al. |
| 2006/0147561 A1 | 7/2006 | Pushpangadan et al. |
| 2006/0172020 A1 | 8/2006 | Djang |
| 2006/0189566 A1 | 8/2006 | Komatsu et al. |
| 2006/0210688 A1 | 9/2006 | Mower |
| 2006/0286259 A1 | 12/2006 | Hargreaves |
| 2007/0020358 A1 | 1/2007 | Mower |
| 2007/0059422 A1 | 3/2007 | Robbins |
| 2007/0082075 A1 | 4/2007 | Xu |
| 2007/0092623 A1 | 4/2007 | Shimizu et al. |
| 2007/0098867 A1 | 5/2007 | Singer |
| 2007/0110850 A1 | 5/2007 | Rifkin |
| 2007/0122496 A1 | 5/2007 | Managoli |
| 2007/0148186 A1 | 6/2007 | Ketzis |

FOREIGN PATENT DOCUMENTS

| | | |
|---|---|---|
| JP | 60-126074 | 7/1985 |
| JP | 08-168354 | 7/1996 |
| JP | 10-108654 | 4/1998 |
| JP | 2000-004852 | 1/2000 |
| JP | 2001-095541 | 4/2001 |
| JP | 2001-245640 | 9/2001 |
| JP | 2006-069948 | 3/2006 |
| WO | 92/06106 | 4/1992 |
| WO | 98/56396 | 12/1998 |
| WO | WO 2005/009351 A2 * | 2/2005 |
| WO | 2005/076750 | 8/2005 |
| WO | 2007/073096 | 6/2007 |

OTHER PUBLICATIONS

Grover et al 2004, Journal of Ethnopharmacology 93: 123-132.*
Taylor, Leslie; Technical Data Report for Bitter Melon (Momordica charantia); Herbal Secrets of the Rainforest, 2002; p. 1-7, Sage Press, Inc.; Thousand Oaks, California.

* cited by examiner

*Primary Examiner* — David H Kruse
(74) *Attorney, Agent, or Firm* — Amin Talati, LLC; George M. Carrera, Jr.; Janine A. Moderson

(57) ABSTRACT

A plant grown from seeds derived from a new interhybrid of three plants of the *Momordica* genus has been cultivated. The new plant hybrid has a faster growth rate than the parent species. Parts of the new interhybrid plant which, when ingested by an individual, have blood glucose and/or insulin regulating properties. Foods and/or beverages containing parts or extracts of the new interhybrid plant and which to promote weight control or loss and/or blood glucose regulation are also disclosed.

8 Claims, No Drawings

CULTIVATED MOMORDICA SPECIES AND EXTRACT THEREOF

This application claims the benefit of earlier filed U.S. Patent Application Ser. No. 60/972,165 filed on 13 Sep. 2007.

FIELD OF THE INVENTION

The present invention relates to a new plant hybrid of the genus *Momordica*, and, more particularly, to a new *Momordica* interhybrid, parts of which can be extracted to produce a material having improved blood sugar and/or insulin regulatory properties in humans.

BACKGROUND

Blood glucose levels play an important role in a person's energy levels and, in general, all bodily functions. A continuous excess of glucose in a person's blood stream is often an indicator of weight and/or blood glucose regulation issues. Generally, an individual's blood glucose levels should fall between about 70 to about 110 mg/ml.

Elevated blood glucose levels (i.e., greater than about 110 mg/dl) typically triggered by alimentary habits, can have a severe impact on an individual's health and can lead to a wide range of problems. For example, diabetes, heart disease, stroke, high blood pressure and blindness are some of the complications that can be derived from prolonged high blood glucose levels. Diabetes, in particular, has been shown to be a precursor of kidney and nervous system disorders and can also cause dental disease and complications of pregnancy.

Blood sugar imbalances attributable to diabetes are typically treated or controlled using insulin or insulin mimetics. For patients who are pre-diabetic and/or are non-insulin dependant, other forms of treatment or intervention may be employed to control blood glucose levels. For example, lifestyle changes that include weight management, nutritional control and/or counseling, and/or exercise regimens may be prescribed or recommended.

However, there is a need and a desire for a product, such as a natural product, that is effective for lowering blood glucose levels. Further, there is a need and a desire for an over-the-counter (OTC) product that can be utilized alone or in combination with other rehabilitative therapies to control blood glucose levels. There is an additional need and a desire for a natural product that can be used to supplement diet and exercise and/or promotes weight loss or control.

In another aspect, a product that is useful for controlling blood glucose and/or insulin levels can be advantageously included in foods and/or beverages used before, during and/or after exercise to maintain steady energy levels and/or hydration. For example, there is a need and a desire for a product or ingredient which promotes the maintenance of steady blood glucose levels that can be used in a sports drink, gel or energy-type food product.

Sports drink formulations generally fall into one of three categories. Isotonic sports drinks are generally designed to help athletes rehydrate as well as to maintain and/or replenish electrolytes such as, for example, sodium, potassium, calcium and magnesium, and other nutrients which can be depleted during strenuous activities. Some isotonic sports drinks may also include carbohydrates such as glucose for energy replenishment.

Another group of sports drinks includes carbohydrate-rich energy drinks. These drinks are specifically designed for use by physically active individuals and are primarily used shortly before or after exercise to boost muscle glycogen stores and help optimize sporting performance. Carbohydrates used in such energy sports drinks are typically derived from sucrose, fructose, glucose polymers, maltodextrin and/or polylactate. Energy sports drinks are less about replacing lost fluid and more about keeping the working muscles supplied with energy during very long and sustained workouts. The disadvantage of energy sports drinks is that their high carbohydrate concentrations tend to slow down the rate of water absorption, particularly during hard exercise.

Recovery sports drinks fall into the third category. Recovery sports drinks are generally taken after exercise and typically include water, carbohydrate and amino acids. Recovery sports drinks may include additional nutrients as electrolytes, minerals, vitamins needed to aid metabolism of the ingested carbohydrate, and protein to promote muscle recovery.

Generally, each of the above sports drinks is designed to provide a particular effect or benefit depending upon the activity an individual is engaged in or the point at which the beverage is ingested, i.e., rehydration during and after strenuous activities where electrolyte loss via perspiration is a concern; energy replenishment during prolonged physical activity; and post-activity muscle recovery. Currently, a sports drink formulation which addresses all three desired benefits, that is rehydration, energy replenishment and muscle recovery support, is not believed to be commercially available. Further, current commercially available sports drinks have not been designed to manage or maintain blood glucose and/or insulin levels, thereby providing an athlete with a steady level of energy throughout a workout or competition In view of the above, there is a need and a demand for a sports drink formulation capable of providing rehydration, energy replenishment, and muscle recovery support in a single formulation. There is further need and a demand for a sports drink formulation having blood sugar and/or insulin regulatory properties.

SUMMARY

A general object of the invention is to provide a naturally-derived product which exhibits blood sugar and/or insulin regulation properties.

The general object of the invention can be obtained, at least in part, through a new plant hybrid of the genus *Momordica* and an extract derived there from. The new *Momordica* interhybrid extract is believed to control or regulate blood sugar and/or insulin levels within the body.

The invention further comprehends a food or beverage product containing the extract derived from the new plant hybrid that assists in the regulation of blood glucose and/or levels and can be utilized to promote weight loss or weight control. One such food or beverage product includes a sports drink which provides a three-fold benefit of rehydration, energy replenishment, and muscle recovery support in a single formulation. A further objective of the invention is to provide a sports drink having blood sugar and/or regulatory properties.

The sports drink formulation can include or consist of:
 a carbohydrate source;
 an amino acid blend;
 a pyruvate blend;
 a mineral blend;
 a *Momordica* sp. extract;
 one or more vitamins; and
 one or more electrolytes.

Other objects and advantages will be apparent to those skilled in the art from the following detailed description taken in conjunction with the examples.

DETAILED DESCRIPTION

The invention provides a sports drink formulation which includes an extract of a newly derived plant hybrid of the genus *Momordica*. The *Momordica* sp. extract and the sports drink formulation including the *Momordica* sp. extract possess blood sugar and/or insulin regulation properties.

Extracts obtained from certain species of the *Momordica* genus have been shown to have a regulatory impact upon blood glucose and/or insulin levels in human subjects. In some cases it is believed that such extracts can successfully restore Beta cells' ability to secrete insulin. In the present invention, a new interhybrid of the genus *Momordica* has been cultivated to have an improved growth rate thereby providing an economical and readily accessible supply of plant material.

The newly derived plant hybrid of the genus *Momordica* (hereinafter the "McB interhybrid") has been stabilized and asexually reproduced. The McB interhybrid is an interhybrid derived from a cross of *Momordica charantia*, commonly known as bitter melon, *Momordica balsamina*, and a previously unnamed Momordica species native to Ecuador. In particular, the McB interhybrid is a tetra-cross pollinated hybrid plant of the aforementioned *Momordica* species.

The McB interhybrid typically produces a seed having a zebra-like striped appearance versus the creamy white, dark brown or spotted seeds of the parent *Momordica* sp. The McB interhybrid further produces a rounded fruit as opposed to the typically elongated fruit of the parents, and has a larger leaf size. Additionally, the McB interhybrid has a faster growth rate than the parent *Momordica* sp.

In one aspect, the McB interhybrid can be derived from a tetra-cross pollination of the three parent *Momordica* species. For example, Species 1 is bred with Species 2 to create Hybrid 1 ($H_1$). Species 1 is also bred with Species 3 to create Hybrid 2 ($H_2$). $H_1$ is crossed with $H_2$ to create Hybrid 3 ($H_3$). Thereafter, $H_1$ is crossed with $H_3$ to derive the new plant hybrid.

An extract of the McB interhybrid may be obtained via extraction of the plant material in a ratio of about 1 gram plant material to about 10 grams of extraction liquid. Typically, such extraction liquid may consist of or include, water, ethanol or a combination thereof. One suitable technique for obtaining a McB extract includes an aqueous soxhlet extraction method.

The sports drink formulation consists of or includes a carbohydrate source, an amino acid blend, a pyruvate blend, a mineral blend, the McB extract, vitamins and/or electrolytes.

The carbohydrate source can be derived from any carbohydrates typically employed in beverages. Such carbohydrate source suitably includes and/or consists of a sugar selected from the group consisting of sucrose, fructose, glucose polymers, maltodextrin, polylactate and combinations thereof. Suitably, the carbohydrate source includes or consists of about 80% to about 95% by weight sugar.

The amino acid blend suitably includes or consists of a branched chain formulation of essential amino acids selected from the group consisting of histidine, isoleucine, leucine, lysine, methionine, phenylalanine, theonine, tryptophan, valine, and combinations thereof.

One suitable amino acid blend includes or consists of:

| | |
|---|---|
| Histidine | 3.9% |
| Isoleucine | 14.1% |
| Leucine | 20.2% |
| Lysine | 12.6% |
| Methionine | 12.4% |
| Phenylalanine | 12.0% |
| Threonine | 7.1% |
| Tryptophan | 3.9% |
| Valine | 13.8% |

The pyruvate blend suitably includes or consists of water soluble calcium pyruvate and sodium pyruvate. Suitably, such pyruvate blend can include or consist of calcium pyruvate blended with sodium pyruvate in a 50:50 ratio.

The mineral blend includes or consists of a combination of macro minerals, essential trace minerals and/or ultra trace minerals. Such macro minerals include or consist of Calcium, Carbon, Chloride, Magnesium, Phosphorus, Potassium, Sodium, Sulfur, and combinations thereof.

Such essential trace minerals include or consist of Chromium, Cobalt, Copper, Iodine, Iron, Manganese, Molybdenum, Selenium, Zinc, and combinations thereof.

Such ultra trace minerals include or consist of Aluminum, Antimony, Arsenic, Barium, Beryllium, Bismuth, Boron, Bromine, Cadmium, Cerium, Cesium, Cobalt, Dysprosium, Erbium, Europium, Fluorine, Gadolinium, Gallium, Germanium, Gold, Hafnium, Holmium, Hydrogen, Indium, Lanthanum, Lead, Lithium, Lutetium, Neodymium, Nickel, Niobium, Nitrogen, Osmium, Oxygen, Palladium, Platinum, Praseodymium, Rhenium, Rhodium, Rubidium, Ruthenium, Samarium, Scandium, Silicon, Silver, Strontium, Tantalum, Tellurium, Terbium, Thallium, Thorium, Thulium, Tin, Titanium, Tungsten, Vanadium, Ytterbium, Yttrium, Zirconium, and combinations thereof.

Vitamins which may be included in the sports drink include and/or consist of vitamin C, vitamin $B_3$, vitamin $B_6$, vitamin $B_{12}$, and combinations thereof.

Electrolytes which may be included in the sports drink formulation include sodium, potassium and combinations thereof. Suitably the sports drink formulation includes or contains sodium in combination with potassium as potassium chloride. Other electrolytes may also be used in the sports drink formulation.

In accordance with one embodiment of the invention, a sports drink formulation having blood sugar and/or insulin regulatory properties includes and/or consists of about 75% to about 90% by weight carbohydrates, about 5% to about 20% by weight amino acids, and about 1% to about 5% by weight of the pyruvate blend, mineral blend, McB extract, vitamins and electrolytes.

The invention may be further understood in connection with the following Example.

EXAMPLE

A sports drink having blood sugar and/or insulin regulatory properties was prepared according to the formulation in TABLE 1. The sports drink provided, in an 8 ounce serving, 85 calories derived from 21 grams of total carbohydrates.

TABLE 1

| Ingredient | Weight |
|---|---|
| Sugar | 20 g |
| Amino Acid Blend | 2.5 g |

TABLE 1-continued

| Ingredient | Weight |
|---|---|
| Pyruvate blend | 50 mg |
| Mineral Blend | 2.5 mg |
| McB Extract | 150 mg |
| Vitamin $B_3$ | 50 mg |
| Vitamin $B_6$ | 2.5 mg |
| Vitamin $B_{12}$ | 0.50 mg |
| Vitamin C | 30 mg |
| Calcium | 25 mg |
| Zinc | 0.25 mg |
| Sodium | 10 mg |
| Potassium chloride | 15 mg |

The amino acid blend is disclosed above in paragraph [0017]. The pyruvate blend is a water soluble blend of calcium and sodium pyruvate in a 50:50 ratio. The mineral blend includes all of the macro minerals, essential trace minerals and ultra trace minerals disclosed above in paragraphs [0019]-[0021]. The McB extract was obtained via aqueous soxhlet extraction of the McB sp. plant material in a ratio of 1 gram plant material per 10 grams water.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

The McB interhybrid seeds of *Momordica*, producing the newly derived plant hybrid and used in the methods disclosed herein were deposited in a quantity of 2500 seeds with the American Type Culture Collection (ATCC®), Patent Depository, 10801 University Boulevard, Manassas, Va. 20110, on Apr. 21, 2011, tested and found to be viable on Jun. 2, 2011, and were accepted on Jun. 3, 2011 and have been assigned Patent Deposit Designation (ATCC Deposit No.) PTA-11843.

We claim:

1. A plant grown from a *Momordica* species interhybrid seed having ATCC accession number PTA-11843 derived from a tetra-cross pollination of parent species *Momordica charantia, Momordica balsamina* and a native Ecuadoran *Momordica* species, the seed having a zebra-like striped appearance,
    wherein the plant grown from the *Momordica* species interhybrid seed has a faster growth rate than any of the parent species.

2. Parts of a plant grown from a *Momordica* species interhybrid seed having ATCC accession number PTA-11843 derived from a tetra-cross pollination of parent species *Momordica charantia, Momordica balsamina* and a native Ecuadoran *Momordica* species.

3. The parts of a plant according to claim 2, wherein the seed produces hybrid plants having a larger leaf size and a more rounded fruit than any one of the parent species.

4. A method of making an extract derived from parts of a plant grown from a *Momordica* species interhybrid seed having ATCC accession number PTA-11843 derived from a tetra-cross pollination of parent species *Momordica charantia, Momordica balsamina* and a native Ecuadoran *Momordica* species, comprising extracting the plant parts with an extraction liquid selected from the group consisting of water, ethanol, and mixtures thereof to provide an extract, the extract having blood glucose regulating properties, insulin regulating properties or a combination thereof.

5. The method according to claim 4, further comprising combining the extract with an edible component.

6. The method according to claim 5, wherein the extract combined with the edible component is a dietary supplement ingestible by an individual to maintain blood glucose levels at a normal level or to reduce blood glucose levels.

7. The method according to claim 4, further comprising combining the extract with at least one beverage component.

8. The method of claim 7, wherein the at least one beverage component comprises:
    a carbohydrate source;
    an amino acid blend;
    a pyruvate blend;
    a mineral blend;
    one or more vitamins; and
    one or more electrolytes.

* * * * *